United States Patent
Park et al.

(10) Patent No.: US 10,431,505 B2
(45) Date of Patent: Oct. 1, 2019

(54) METHOD OF INSPECTING SURFACE HAVING A MINUTE PATTERN BASED ON DETECTING LIGHT REFLECTED FROM METAL LAYER ON THE SURFACE

(71) Applicant: Samsung Electronics Co., Ltd., Suwon-si, Gyeonggi-do (KR)

(72) Inventors: Jun-bum Park, Goyang-si (KR); Kyung-sik Kang, Bucheon-si (KR); Byeong-hwan Jeon, Yongin-si (KR); Jae-chol Joo, Suwon-si (KR); Tae-joong Kim, Hwaseong-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 7 days.

(21) Appl. No.: 15/429,525

(22) Filed: Feb. 10, 2017

(65) Prior Publication Data

US 2017/0352599 A1    Dec. 7, 2017

(30) Foreign Application Priority Data

Jun. 7, 2016    (KR) .................... 10-2016-0070310

(51) Int. Cl.
  *G01J 3/42*      (2006.01)
  *H01L 21/66*     (2006.01)
  *G01N 21/27*     (2006.01)
  *G01N 21/95*     (2006.01)
  *G01N 21/956*    (2006.01)
  (Continued)

(52) U.S. Cl.
  CPC .............. *H01L 22/12* (2013.01); *G01J 3/42* (2013.01); *G01N 21/27* (2013.01); *G01N 21/553* (2013.01); *G01N 21/9505* (2013.01); *G01N 21/95607* (2013.01); *H01L 21/32051* (2013.01); *G01J 2003/2833* (2013.01); *G01N 2021/258* (2013.01); *H01L 22/24* (2013.01)

(58) Field of Classification Search
  CPC ........................................................ H01L 22/12
  USPC ....................................................... 356/445
  See application file for complete search history.

(56) References Cited

U.S. PATENT DOCUMENTS 6,045,433 A * 4/2000 Dvir ..................... B24B 37/005
                                                257/E21.525
6,479,309 B1    11/2002 Wright
(Continued)

FOREIGN PATENT DOCUMENTS

JP    2007164061 A    6/2007
JP    4035016 B2      1/2008
(Continued)

*Primary Examiner* — Roy M Punnoose
(74) *Attorney, Agent, or Firm* — Harness, Dickey & Pierce P.L.C.

(57) ABSTRACT

Manufacturing a device may include inspecting a surface of an inspection target device. The inspecting may include forming a metal layer on a surface of the inspection target device on which a minute pattern is formed, directing a beam of light to be incident and normal to the surface of the inspection target device, determining a spectrum of light reflected from the surface of the inspection target device, and generating, via the spectrum, information associated with a structural characteristic of the minute pattern formed on the inspection target device. The inspection target device may be selectively incorporated into the manufactured device based on the generated information.

11 Claims, 11 Drawing Sheets

(51) Int. Cl.
  *H01L 21/3205*  (2006.01)
  *G01N 21/552*  (2014.01)
  *G01J 3/28*  (2006.01)
  *G01N 21/25*  (2006.01)

(56) References Cited

U.S. PATENT DOCUMENTS

| | | | |
|---|---|---|---|
| 6,690,473 B1* | 2/2004 | Stanke | B24B 37/34 |
| | | | 257/E21.53 |
| 6,891,627 B1 | 5/2005 | Levy et al. | |
| 7,019,850 B2* | 3/2006 | Finarov | G01B 11/0625 |
| | | | 356/237.4 |
| 7,123,366 B2* | 10/2006 | Scheiner | G01B 11/02 |
| | | | 356/625 |
| 7,187,456 B2* | 3/2007 | Scheiner | G01B 11/02 |
| | | | 250/559.28 |
| 7,499,183 B2 | 3/2009 | Maznev | |
| 7,595,896 B2* | 9/2009 | Cohen | G01B 11/0625 |
| | | | 356/630 |
| 8,179,530 B2 | 5/2012 | Levy et al. | |
| 9,140,652 B2 | 9/2015 | Naya et al. | |
| 9,494,529 B1* | 11/2016 | Fresquet | G02B 21/0032 |
| 2002/0005957 A1* | 1/2002 | Finarov | B24B 37/013 |
| | | | 356/630 |
| 2002/0128784 A1* | 9/2002 | Scheiner | G01B 11/02 |
| | | | 702/57 |
| 2003/0086097 A1* | 5/2003 | Finarov | G01B 11/0625 |
| | | | 356/630 |
| 2004/0038139 A1* | 2/2004 | Mui | G03F 7/70625 |
| | | | 430/30 |
| 2004/0042017 A1* | 3/2004 | Cohen | G01B 11/0625 |
| | | | 356/630 |
| 2005/0062965 A1* | 3/2005 | Scheiner | G01B 11/02 |
| | | | 356/319 |
| 2005/0146729 A1* | 7/2005 | Scheiner | G01B 11/02 |
| | | | 356/504 |
| 2005/0231713 A1* | 10/2005 | Owen | G01N 21/8806 |
| | | | 356/237.1 |
| 2006/0176494 A1* | 8/2006 | Finarov | G01B 11/0625 |
| | | | 356/630 |
| 2013/0182248 A1 | 7/2013 | Naya et al. | |
| 2016/0047744 A1* | 2/2016 | Adel | G03F 7/70633 |
| | | | 356/401 |
| 2016/0116420 A1* | 4/2016 | Duffy | G03F 7/70625 |
| | | | 702/155 |

FOREIGN PATENT DOCUMENTS

| | | |
|---|---|---|
| JP | 5553717 B2 | 7/2014 |
| KR | 19970060095 A | 8/1997 |
| KR | 20020037441 A | 5/2002 |
| KR | 20060024435 A | 3/2006 |
| KR | 20150035035 A | 4/2015 |

\* cited by examiner

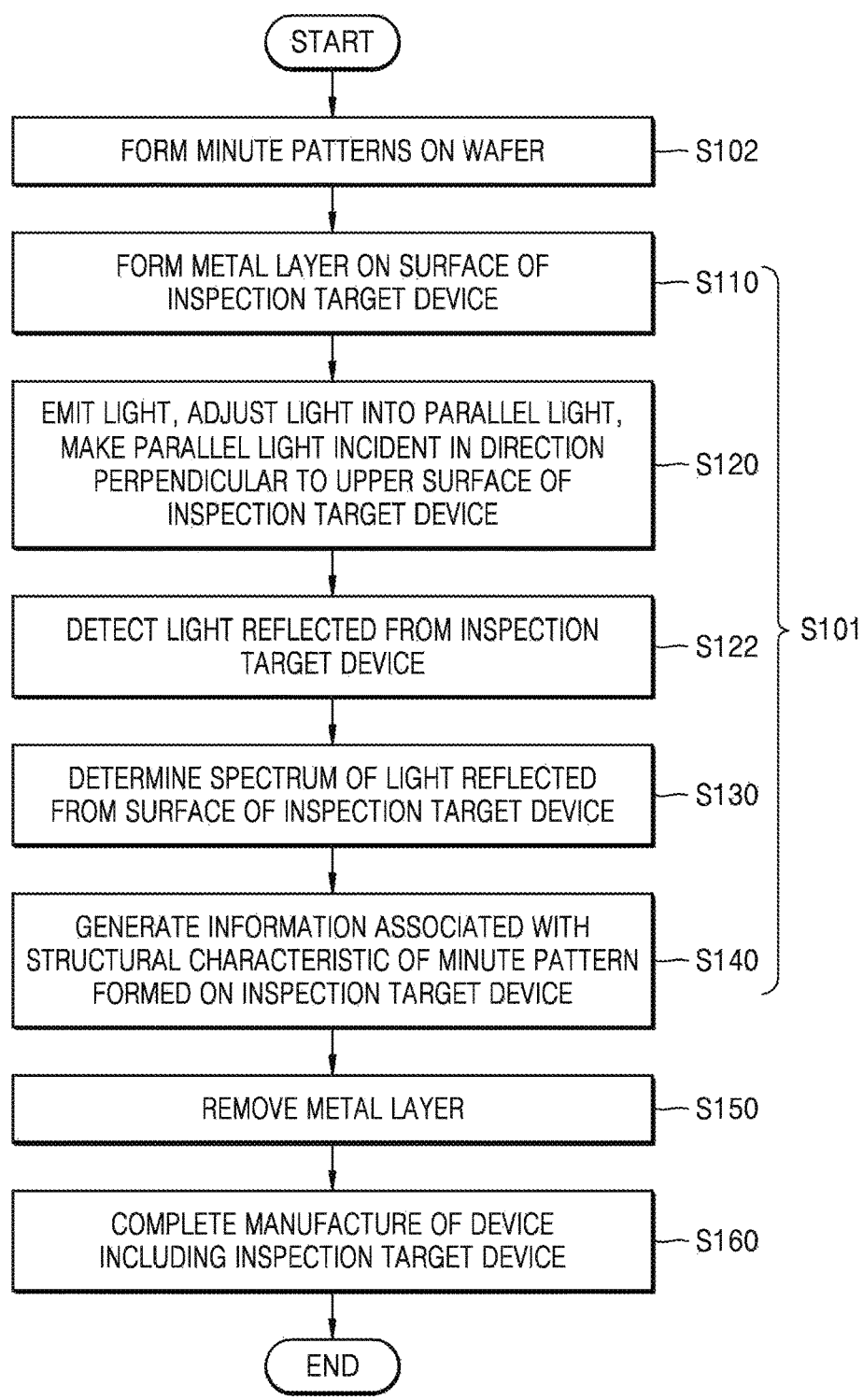

METHOD OF INSPECTING SURFACE HAVING A MINUTE PATTERN BASED ON DETECTING LIGHT REFLECTED FROM METAL LAYER ON THE SURFACE

CROSS-REFERENCE TO RELATED APPLICATIONS

This application claims the benefit of Korean Patent Application No. 10-2016-0070310, filed on Jun. 7, 2016, in the Korean Intellectual Property Office, the disclosure of which is incorporated herein in its entirety by reference.

BACKGROUND

The inventive concepts relate to inspecting a surface, and more particularly, to optical methods of inspecting a surface.

In manufacturing processes for manufacturing semiconductor devices, a designed pattern has to be accurately formed on the semiconductor devices in each manufacturing process. To inspect such a designed pattern, a method of manufacturing semiconductor devices that includes optically observing a shape of a semiconductor device has been used.

In some cases, according to this method, there may be a lower limit upon the size of patterns that may be inspected (e.g., nano-level patterns), and thus, an accurate analysis of nano-level patterns may be difficult.

Accordingly, a method of manufacturing semiconductor devices that includes a surface method, that is, an optical method capable of inspecting nano-level patterns have to be developed.

SUMMARY

Some example embodiments of the inventive concepts provide a surface inspection method for inspecting a nano-level pattern formed on an inspection target object so that inspection expenses may be reduced.

According to some aspects of the inventive concepts, a method may include: forming a metal layer on the surface of an inspection target device, the inspection target device including a minute pattern, such that the metal layer is formed on the minute pattern and an outer surface of the metal layer is distal to the surface of the inspection target device; emitting light incident on the outer surface of the metal layer, and adjusting the emitted light to be incident to the outer surface of the metal layer and normal to the outer surface of the metal layer; detecting a spectrum of the light reflected from the outer surface of the metal layer; and generating, based on the detected spectrum, information associated with a structural characteristic of the minute pattern formed on the surface of the inspection target device.

According to some aspects of the inventive concepts, a method may include: forming an inspection auxiliary layer on a surface of a wafer; generating surface plasmon resonance (SPR) on the inspection auxiliary layer based on emitting light incident on the inspection auxiliary layer, the emitted light being normal to the inspection auxiliary layer; detecting light reflected from the inspection auxiliary layer; determining a reflectivity of the surface of the wafer, based on a wavelength of the detected light reflected from the surface of the wafer; and generating, based on the determined reflectivity, information associated with a structural characteristic of a pattern on the wafer.

According to some aspects of the inventive concepts, a method may include: detecting light reflected from a surface of an inspection target device, the surface of the inspection target device including at least one minute pattern, the surface including a surface of a metal layer on the inspection target device, the reflected light being a reflected beam of light incident on the surface of the inspection target device, the beam of light being normal to the surface of the inspection target device; determining a spectrum of the light reflected from the surface of the inspection target device; generating, based on the determined spectrum, information associated with a structural characteristic of the minute pattern on the surface of the inspection target device; and forming a semiconductor device, using the inspection target device, based on the information associated with the structural characteristic of the minute pattern.

BRIEF DESCRIPTION OF THE DRAWINGS

Example embodiments of the inventive concepts will be more clearly understood from the following detailed description taken in conjunction with the accompanying drawings in which:

FIG. 1 is a flowchart of a method of manufacturing a device, according to some example embodiments of the present inventive concepts;

DETAILED DESCRIPTION OF THE EMBODIMENTS

Figure 2A:
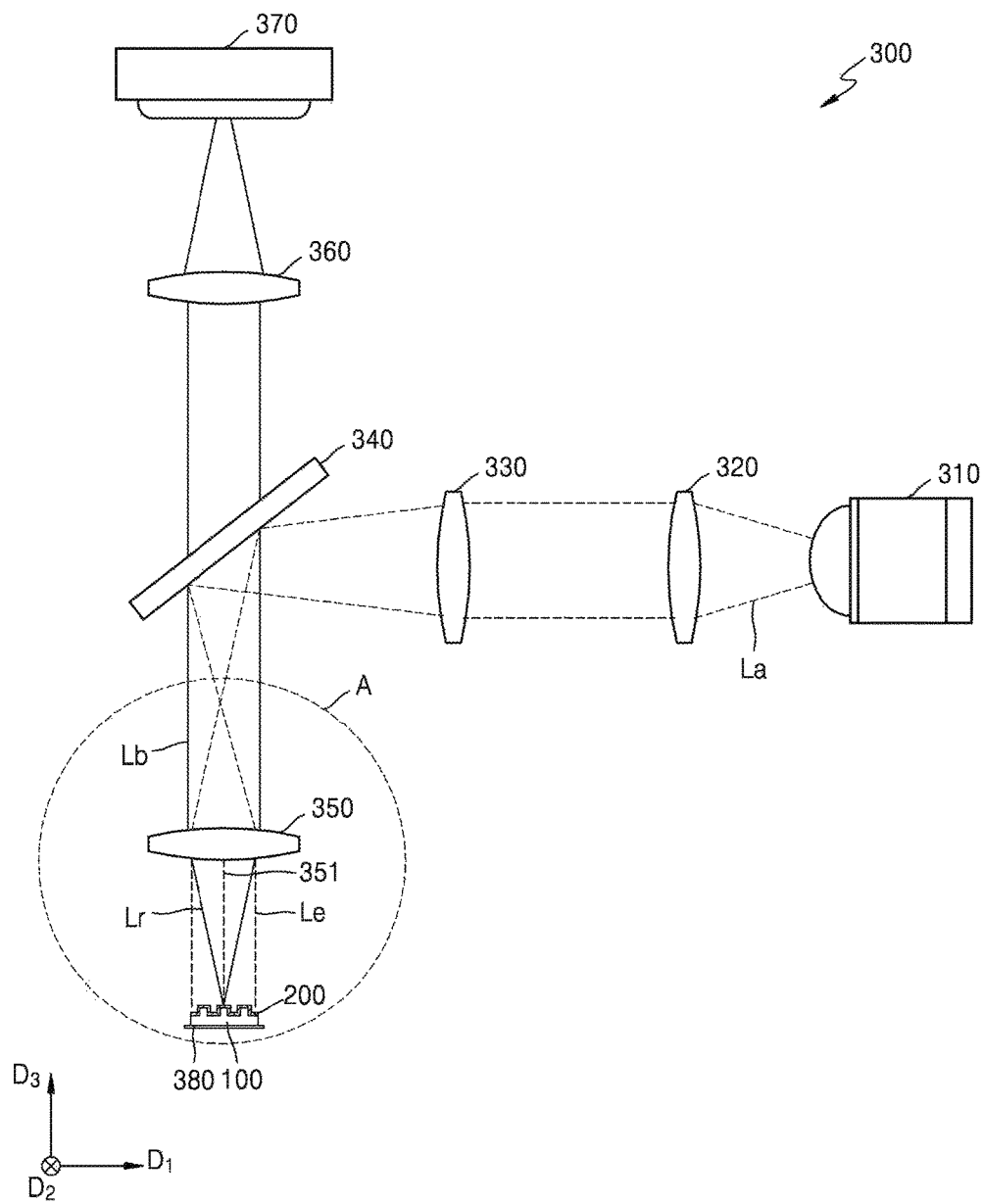
FIG. 2A is a schematic view of a surface inspection apparatus used along with a method of manufacturing a device that includes inspecting a surface according to some example embodiments of the present inventive concepts, and an inspection target device to which the method according to some example embodiments of the present inventive concepts is applied.

Unless otherwise defined, all terms used herein have the same meaning as commonly understood by one of ordinary skill in the art to which embodiments belong.

Hereinafter, example embodiments of the present inventive concepts will be described in detail by referring to the accompanying drawings.

FIG. 1 is a flowchart of a method of manufacturing a device, according to some example embodiments of the present inventive concepts.

Referring to FIG. 1, the method according to some example embodiments may include forming ("manufacturing") minute patterns on inspection target device (S102). The method may include inspecting a surface of the inspection target device (S101). As shown in FIG. 1, the inspecting (S101) may include forming (S110) a metal layer on a surface of the inspection target device on which a minute pattern is formed, emitting (S120) light for inspecting the surface, adjusting the emitted light into parallel light, and making the parallel light incident in a direction perpendicular to an upper surface of the inspection target device. Here, the light used for inspection may be light having a broadband wavelength. Thus, in order to reduce and/or minimize spectrum distortion due to oblique illumination, the light may be incident in a direction perpendicular to (e.g., normal to) an upper surface of the inspection target device. The inspecting S101 may include detecting (S122) light reflected from the surface of the inspection target device, determining (S130) a spectrum of light (e.g., wavelength spectrum of light) reflected from the surface of the inspection target device and generating (S140) information associated with a structural characteristic of one or more minute patterns formed on the inspection target device, based on the spectrum. A minute pattern may include a plurality of patterns that are periodically formed on the inspection target device. The information associated with the structural characteristic of the minute pattern may include information indicating whether neighboring minute patterns are similar to one another, or information indicating a width and a depth associated with one or more minute patterns, and a distance ("interval") between adjacent minute patterns.

If and/or when the inspection target device is a semiconductor device, the forming (S102) may include manufacturing the semiconductor device. In some example embodiments, the forming may include forming one or more layers on a substrate, at least partially removing (e.g., etching) one or more layers to form a pattern in the semiconductor device, some combination thereof, or the like.

As shown in FIG. 1, the method according to some example embodiments may include removing the metal layer (S150), subsequent to the inspecting (S101). As further shown in FIG. 1, the method according to some example embodiments may include manufacturing a device using the inspection target device (S160), subsequent to the inspecting (S101). The device manufactured at (S160) may include one or more of a semiconductor device, computer device, electronic device, some combination thereof, or the like. In some example embodiments, the inspection target device may be selectively incorporated into the manufacturing of the device at (S160) based on the information generated at (S140).

Figure 2B:
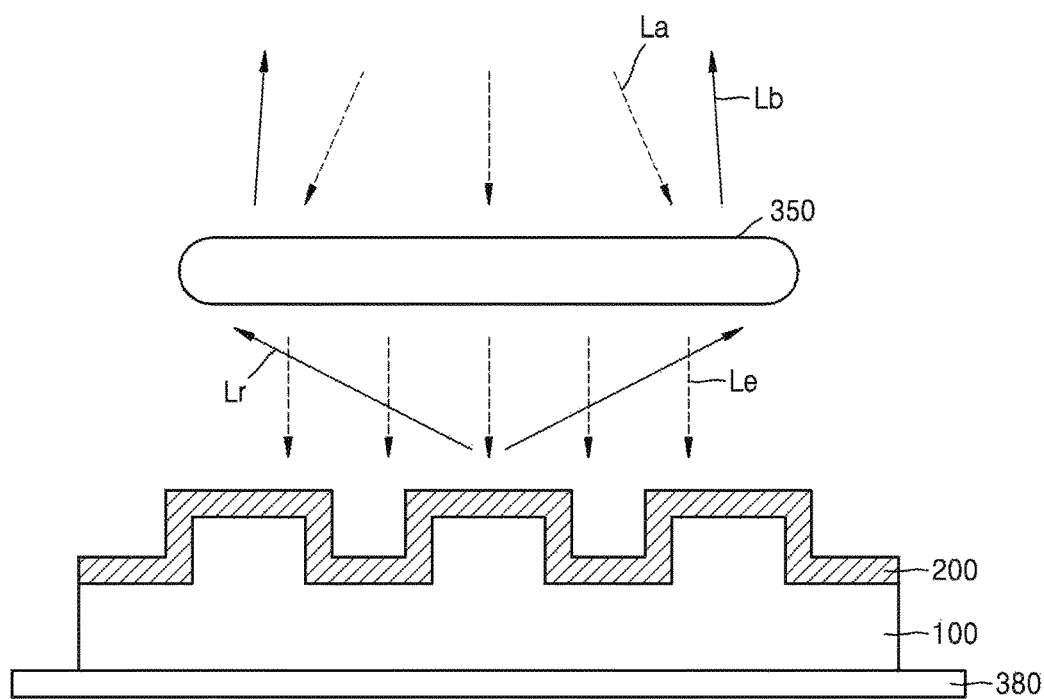
FIG. 2B is an enlarged schematic view of portion A of FIG. 2A.

FIG. 2A is a schematic view of a surface inspection apparatus used along with a method of manufacturing a device that includes inspecting a surface according to some example embodiments of the present inventive concepts, and an inspection target device to which the method according to some example embodiments of the present inventive concepts is applied. FIG. 2B is an enlarged schematic view of portion A of FIG. 2A.

Referring to FIG. 2A, the surface inspection apparatus 300 according to some example embodiments may include a broadband light source 310, first and second condensing lenses 320 and 330 concentrating light La emitted from the broadband light source 310, a beam splitter 340, an objective lens 350, a tube lens 360 configured to concentrate light Lr reflected from the inspection target device 100, a detector 370 configured to detect information associated with the inspection target device 100, and a stage 380 supporting the inspection target device 100. The surface inspection apparatus 300 may be disposed in a chamber maintained as a uniform temperature.

The broadband light source 310 may emit the light La. The broadband light source 310 may be a point light source, and when the light La is diffused and emitted via the point light source, the light La may be adjusted as parallel light Le via the objective lens 350. The broadband light source 310 may be a white light source, but is not limited thereto. The light La may be transmitted to the first and second condensing lenses 320 and 330.

The beam splitter 340 may reflect the light La emitted from the broadband light source 310 and transmitted via the first and second condensing lenses 320 and 330, and transmit the reflected light La to the objective lens 350. Also, the beam splitter 340 may have light Lb reflected from the inspection target device 100 and transmitted via the objective lens 350 penetrate the beam splitter 340 and may transmit the light Lb to the detector 370 via the tube lens 360.

The objective lens 350 may adjust the light La emitted from the broadband light source 310 and transmitted via the beam splitter 340 as the parallel light Le. Accordingly, a section of the light Le may have a certain area, and the light Le may be irradiated onto a relatively large area of the inspection target device 100. The objective lens 350 may concentrate the light Lr reflected from the inspection target device 100 on which the metal layer 200 is formed, and transmit the light Lr to the beam splitter 340.

The detector 370 is a device configured to receive the light Lr and convert the light Lr into an electrical signal. The detector 370 may include photoelectric devices, such as a charge coupled device (CCD), a complementary metal-oxide semiconductor (CMOS), and a photomultiplier tube (PMT). The detector 370 may include a wavelength response analyzer. The wavelength response analyzer may analyze a wavelength of the light Lr reflected from the inspection target device 100 and analyze a reflectivity and/or reflectance of the inspection target device 100 (e.g., a reflectivity and/or reflectance of a surface 102 of the inspection target device 100) based on the wavelength of the light Lr. That is, the wavelength response analyzer may analyze a spectrum of the light Lr. By doing so, the wavelength response analyzer may generate information associated with a structural characteristic of one or more minute patterns formed on the inspection target device 100. The wavelength response analyzer may determine whether neighboring ("adjacent") minute patterns are similar to one another, and/or may measure a width and a depth associated with one or more minute patterns, and/or a distance between adjacent minute patterns.

The stage 380 may support the inspection target device 100. The stage 380 may move in a longitudinal direction and a traverse direction to shift the inspection target device 100 to a position in which a desired area thereof may be measured. For example, the stage 380 may move the inspection target device 100 along a plane that extends orthogonally to an axis 351 of the objective lens 350, including along one of directions D1 and D2, such that different portions of the device 100 may be aligned with the axis 351. Axis 351 may be a central axis of the objective lens 350. The stage 380 may be restricted from moving the inspection target device 100 along direction D3.

Referring to FIGS. 2A and 2B, the metal layer 200 may be formed on the inspection target device 100. If and when light is incident onto the inspection target device 100, surface plasmon resonance (SPR) may occur on the metal layer 200. There may be a plasmon regionally on a surface in a structure of a nanometer size, and the plasmon may be combined with light to generate the SPR. In some example embodiments, the SPR may result in a wavelength increase in at least some of the light reflected from the inspection target device 100, relative to the light that is incident on the inspection target device 100. A surface inspection apparatus may be configured to inspect minute patterns on the inspection target device 100 with greater accuracy and/or precision based on the increased wavelength of light reflected from the inspection target device 100, where the increased wavelength of the reflected light is based on the metal layer 200 formed on the inspection target device 100. For example, the surface inspection apparatus may be configured to detect and/or inspect smaller (minuter) patterns on the inspection target device 100 based on the increased wavelength of light reflected from the inspection target device 100 due to the metal layer 200, relative to the size of patterns on the inspection target device 100 that may be detected and/or inspected by the surface inspection apparatus if and/or when the metal layer 200 is absent from the inspection target device 100.

The metal layer 200 is formed to improve surface inspection of the inspection target device 100. In some example embodiments, the metal layer 200 may include at least one of Au, Ag, Cu, and Al. The metal layer 200 may be formed via chemical vapor deposition (CVD), physical vapor deposition (PVD), atomic layer deposition (ALD), sputtering, E-beam deposition, thermal deposition, etc. The metal layer 200 may be formed via a combination of the processes, or may be formed via any single process. In particular, the metal layer 200 may be deposited on a surface 101 of the inspection target device 100 by using a focused ion beam (FIB) gun.

The light Le used for inspection may be light having a broadband wavelength. When the light La is diffused and emitted from the broadband light source 310, the light La may be adjusted as the parallel light Le via the objective lens 350. The light Le adjusted to be parallel may be incident in a direction perpendicular to an upper surface 102 of the inspection target device 100 (e.g., incident on the upper surface 102 and normal to the upper surface 102) in order to minimize spectrum distortion due to oblique light.

Figure 3:
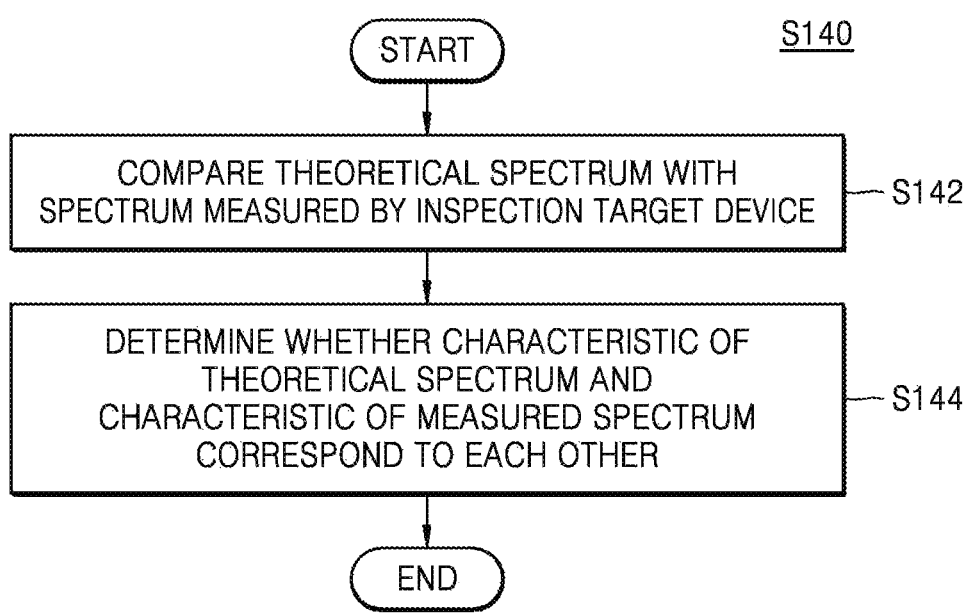
FIG. 3 is a flowchart of a method, according to some example embodiments of the present inventive concepts, and more particularly, a detailed flowchart of operation S140 of FIG. 1.

FIG. 3 is a flowchart of a method, according to some example embodiments of the present inventive concepts, and more particularly, a detailed flowchart of operation S140 of FIG. 1.

Referring to FIG. 3, a method of manufacturing a device that includes inspecting a surface thereof according to some example embodiments may include generating (S140) information associated with a structural characteristic of the minute pattern. The generating (S140) may include comparing (S142) a theoretical spectrum of a theoretical model with a spectrum measured at the inspection target device 100, and determining (S144) whether a characteristic of the theoretical spectrum and a characteristic of the measured spectrum correspond to each other.

The theoretical model may be a sample on which surface inspection is performed before inspecting (S101) a surface 102 of the inspection target device 100, and the sample may have a minute pattern having the same shape (e.g., a common shape) or substantially the same shape (e.g., the same shape within manufacturing tolerances and/or material tolerances) as the minute pattern formed on the inspection target device 100. A surface inspection result according to a structural characteristic of the theoretical model may be stored in a library.

After the method of inspecting a surface according to some example embodiments is performed and a spectrum is derived from the inspection target device 100, spectrum data associated with the theoretical model stored in the library and the measured spectrum may be compared with each other. Via this comparison, a determination may be made regarding whether a theoretical result of the theoretical model and a measured result of the inspection target device 100 correspond to each other. In some example embodiments, results that correspond to each other may include results that match within a particular margin (e.g., 10% margin of error between theoretical results and measured results). In some example embodiments, results that correspond to each other include results that are the same or substantially the same (e.g., the same within manufacturing tolerances and material tolerances).

Based on a determination that the theoretical result is corresponds to the measured result, the information associated with the structural characteristic of the minute pattern formed on the inspection target device 100 may be generated.

In some example embodiments, an inspection target device 100 may be selectively incorporated into the manufacture of a device at (S160) based on the generated information. For example, the inspection target device 100 may be incorporated into the manufacturing of the device at (S160), such that the inspection target device 100 is incorporated into the manufactured device, based on information generated at (S140) according to a determination that a theoretical result of the theoretical model and a measured result of the inspection target device 100 correspond to each other. In another example, the inspection target device 100 may be restricted from being incorporated into the manufacturing of the device at (S160), such that the inspection target device 100 is not incorporated into the manufactured device, based on information generated at (S140) according to a determination that a theoretical result of the theoretical model and a measured result of the inspection target device 100 do not correspond to each other.

Figure 4A:
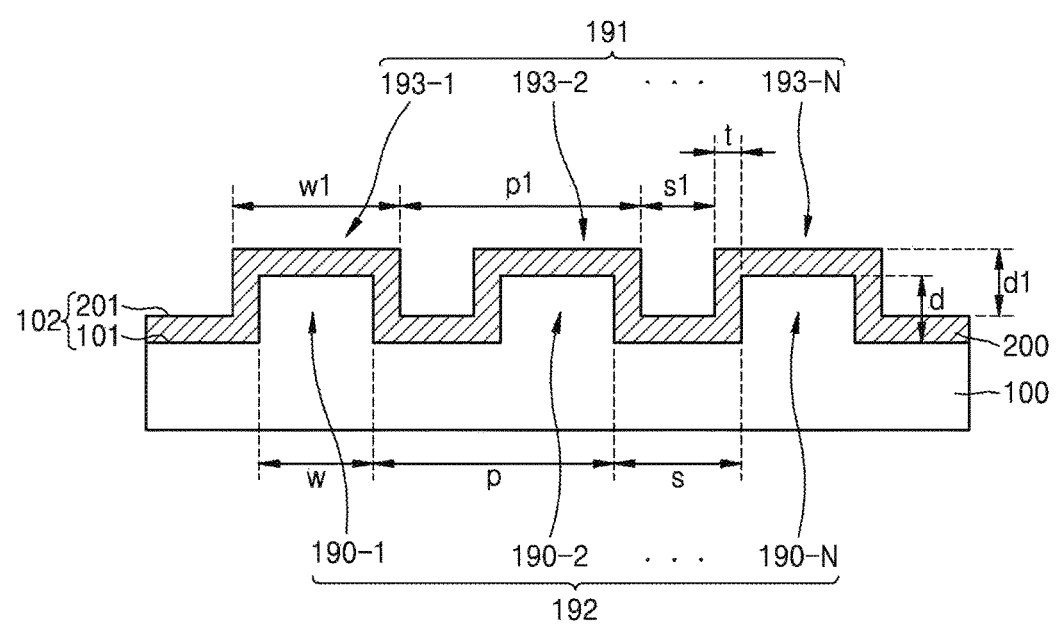
FIG. 4A is a cross-sectional view of an inspection target device according to some example embodiments of the present inventive concepts.
Figure 4B:
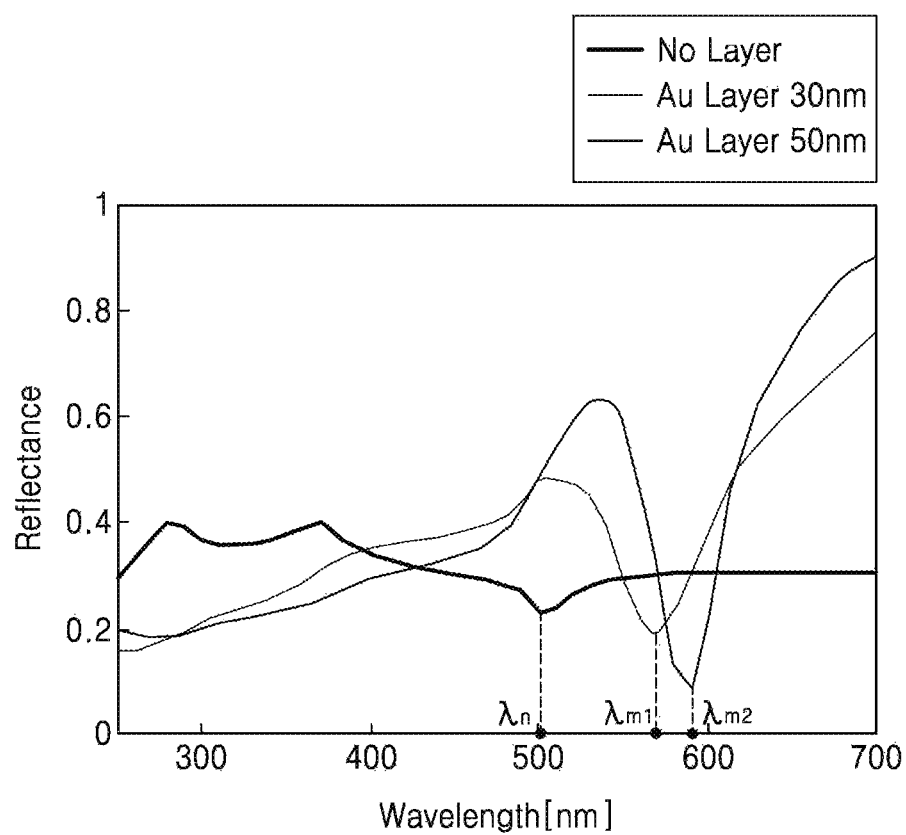
FIG. 4B is a graph of a spectrum measured based on inspecting a surface, according to some example embodiments of the present inventive concepts.

FIG. 4A is a cross-sectional view of an inspection target device according to some example embodiments of the present inventive concepts. FIG. 4B is a graph of a spectrum measured based on inspecting a surface, according to some example embodiments of the present inventive concepts.

Referring to FIG. 4A, a minute pattern 192 may be formed on the inspection target device 100, such that the inspection target device 100 includes the minute pattern 192. As shown in FIG. 4A, the minute pattern 192 may include a set of one or more patterns 190-1 to 190-N that are periodically formed on the surface 101 of the inspection target device 100. The minute pattern 192 may include a line and space pattern and may have a shape of a lattice. One or more minute patterns 190-1 to 190-N may have a certain depth d and a width s. The minute patterns 190-1 to 190-N may be repeatedly formed to have a certain period p (e.g., "interval) between adjacent minute patterns 190-1 to 190-N. A method that includes inspecting a surface 102 according to some example embodiments may include measuring the width w and the depth d of one or more of the minute patterns 190-1 to 190-N, and the distance s between adjacent minute patterns 190-1 to 190-N of the minute pattern 192 formed on the inspection target device 100.

The metal layer 200 may be formed on a surface 101 of the inspection target device 100. The metal layer 200 is formed along the surface 101 of the inspection target device 100, and thus, the metal layer 200 may also have a minute pattern 191 having a certain period p1. The minute pattern 191 may include one or more minute patterns 193-1 to 193-N that correspond to separate, respective minute patterns 190-1 to 190-N formed on the inspection target device 100. A thickness t of the metal layer 200 may be less than a half the distance s between the minute patterns formed on the inspection target device 100. If and/or when the thickness t of the metal layer 200 is equal to or greater than half the distance s between the minute patterns 190-1 to 190-N formed on the inspection target device 100, the metal layer 200 may not have the minute pattern 191. If and/or when the metal layer 200 does not have the minute pattern 191, even if light for surface inspection of the inspection target device 100 is irradiated onto the metal layer 200, it may be difficult to obtain the information associated with the structural characteristic of the minute pattern 190 formed on the inspection target device 100.

As shown in FIG. 4A, the upper surface 102 of the inspection target device 100 may include one or more of the upper surface 101 of the inspection target device 100 and/or the upper surface 201 of the metal layer 200 formed on surface 101 of the inspection target device 100. As shown in FIG. 4A, the upper surface 201 of the metal layer 200 is distal to the upper surface 101 of the inspection target device 100 on which the metal layer 200 is formed. As referred to herein, directing light to, and/or reflecting light from, a surface 102 of the inspection target device 100 may include directing light to and reflecting light from one or more of surfaces 101 and 201.

Here, if and/or when light is irradiated onto the inspection target device 100 (e.g., a beam of light is incident on the inspection target device 100) in a state in which the metal layer 200 is formed on the inspection target device 100 and a spectrum of detected light reflected from surface 102 of the inspection target device 100 is obtained ("determined"), an error may occur due to the metal layer 200. That is, a result of measuring a width w1 and a depth d1 of the minute patterns 193-1 to 193-N and a distance s1 between the minute patterns 191 formed on the metal layer 200 may be derived.

Thus, in order to generate the information associated with the structural characteristic of the minute pattern 192 formed on the inspection target device 100, the error due to the metal layer 200 may be calculated, and the information associated with the structural characteristic of the minute pattern 192 may be determined based on the calculated error and the determined spectrum of detected light reflected from surface 102 of the inspection target device 100. The error due to the metal layer 200 may be calculated based on the width w and the depth d of the minute pattern 192 of the inspection target device 100, the distance s between the minute patterns 190-1 to 190-N thereof, a thickness of the metal layer 200, a material of the metal layer 200, some combination thereof, etc.

Referring to FIGS. 4A and 4B, a reflectivity associated with surface 102 of the inspection target device 100 (e.g., reflectivity of the surface 102, reflectivity associated with light reflected from surface 102, etc.) may be determined, based on a wavelength of the light reflected from surface 102, when the metal layer 200 is formed on the surface 101 of the inspection target device 100 and when the metal layer 200 is not formed on the surface 101 of the inspection target device 100. The metal layer 200 may include gold.

In the surface inspection (S101), the information associated with the structural characteristic of the minute pattern 192 formed on the inspection target device 100 may be generated based on wavelength values $\lambda n$, $\lambda m1$, $\lambda m2$ in which the reflectivity associated with surface 102 of the inspection target device 100 has a lowest value. The structural characteristic of the minute pattern 192 may include the width w of one or more minute patterns 190-1 to 190-N and the distance s between adjacent minute patterns 190-1 to 190-N.

When comparing the reflectivity based on the light reflected from the inspection target device 100, the wavelength value $\lambda m1$ in which the reflectivity has the lowest value when the metal layer 200 is formed may be greater than the wavelength value $\lambda n$ in which the reflectivity has the lowest value when the metal layer 200 is not formed. That is, due to a surface plasmon effect generated on the metal layer 200, the wavelength value in which the reflectivity associated with the surface 102 has the lowest value increases. When comparing the wavelength values $\lambda m1$ and $\lambda m2$ in which the reflectivity has the lowest value when the metal layer 200 is formed, the wavelength value in which the reflectivity has the lowest value increases as the thickness of the metal layer 200 may be changed from 30 nm to 50 nm. That is, as the thickness of the metal layer 200 increases, the wavelength value in which the reflectivity has the lowest value may increase. This is because as the thickness of the metal layer 200 increases, transmittance loss of the light used for surface inspection is reduced and most of the light contributes to generation of the plasmon effect.

Generally, as the width w of the minute pattern 192 formed on the inspection target device 100 decreases, the wavelength value in which the reflectivity has the lowest value decreases. Thus, in order to inspect the inspection target device 100 on which the minute pattern 192 is formed, a wavelength area which the surface inspection apparatus may analyze may be decreased, and thus, a surface inspection apparatus previously used may have to be replaced. In some example embodiments, if and/or when the metal layer 200 is formed on the inspection target device 100, compared to when the metal layer 200 is not formed on the inspection target device 100, the wavelength value in which the reflectivity has the lowest value is increased. This may be based at least in part upon a surface plasmon effect (e.g., SPR) generated if and/or when light is irradiated on the surface 201 of the metal layer 200. Thus, even if the minute pattern 192 formed on the inspection target device 100 becomes minuter (e.g., smaller), a surface inspection apparatus may be configured to be used to measure the width w of the minute pattern 192 and the distance s between the minute patterns 190-1 to 190-N, based on the metal layer 200 applied to the inspection target device 100. The thickness of the metal layer 200 may be adjusted by a user configuration, and as the metal layer 200 has a greater thickness, a change in the wavelength value in which the reflectivity has the lowest value may increase. In some example embodiments, in this case, the width w of one or more minute patterns 190-1 to 190-N formed on the inspection target device 100 may be limited.

In some example embodiments, according to the graph of FIG. 4B, if and/or when the metal layer 200 is formed, a change in the reflectivity of surface 102 of the inspection target device 100, determined based on the wavelength of the light reflected therefrom, may be more radical than a change in reflectivity of surface 102 of the inspection target device if and/or when the metal layer 200 is not formed on the surface 101 of the inspection target device 100. Such a change may be based at least in part upon a surface plasmon effect, including SPR. As the change in the reflectivity based on the wavelength is more radical, the surface inspection apparatus may more easily detect the wavelength value in which the reflectivity of surface 102 of the inspection target device 100 has the lowest value, thereby effectively enabling inspection of the surface 102 of the inspection target device 100. Thus, inspection of the inspection target device 100 may be improved based on inspecting the inspection target device 100 in and/or when the metal layer 200 has been formed thereon.

Figure 5A:
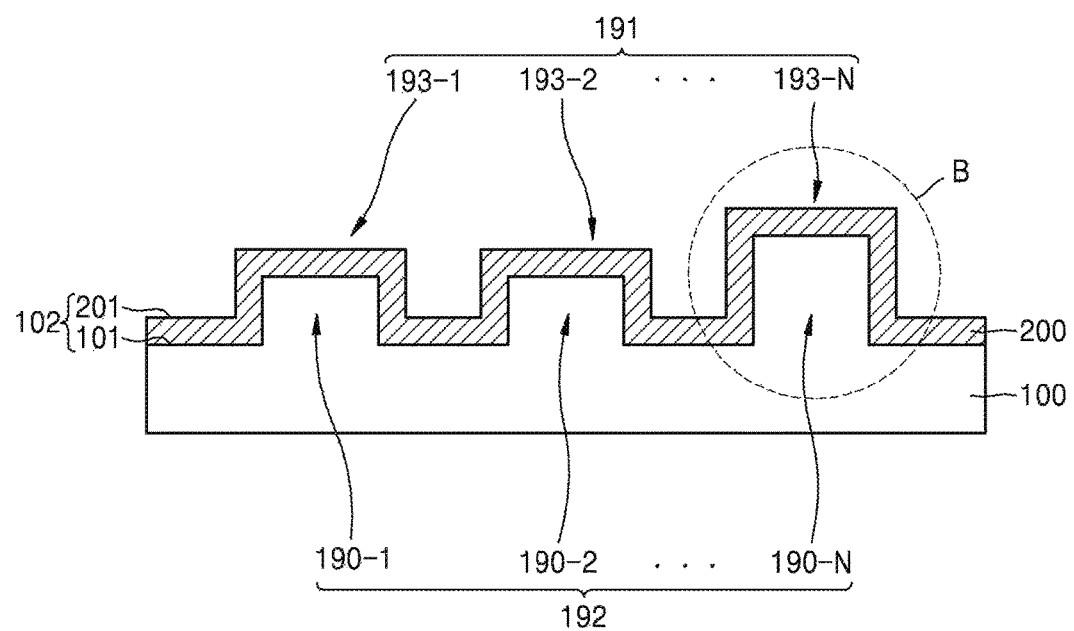
FIG. 5A is a cross-sectional view of an inspection target device according to some example embodiments of the present inventive concepts.
Figure 5B:
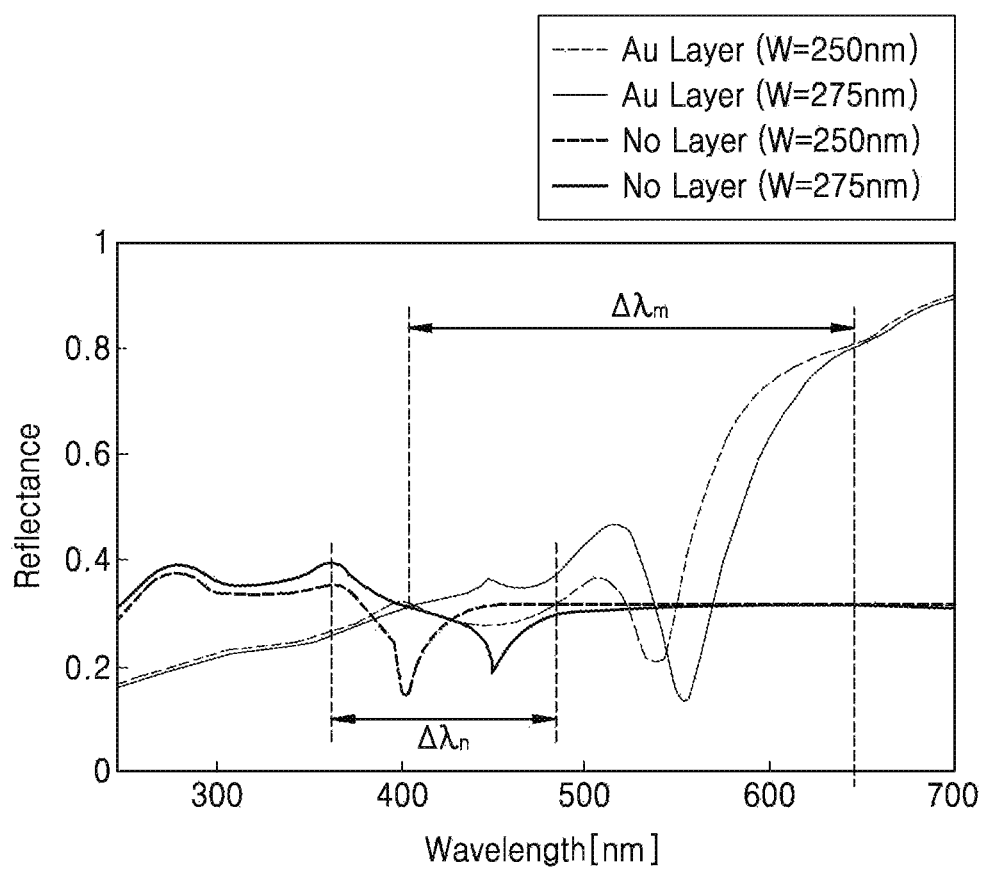
FIG. 5B is a graph of a spectrum measured by using a method according to some example embodiments of the present inventive concepts.

FIG. 5A is a cross-sectional view of an inspection target device according to some example embodiments of the present inventive concepts. FIG. 5B is a graph of a spectrum measured by using a method according to some example embodiments of the present inventive concepts.

Referring to FIG. 5A, the metal layer 200 may be formed on a surface 101 of the inspection target device 100 to which the method of inspecting a surface 102 according to the present inventive concepts is applied. Also, a minute pattern 192 may be formed on the inspection target device 100. The minute pattern 192 may include a plurality of patterns 190-1 to 190-N that are periodically formed. The minute patterns 190-1 to 190-N may have the same shape, but one or more B of the minute patterns 190-1 to 190-N may have different shapes from neighboring ("adjacent") minute patterns 190-1 to 190-N. Thus, inspecting a surface 102 according to some example embodiments may include determining whether neighboring minute patterns 190-1 to 190-N are similar to one another.

Referring to FIGS. 5A and 5B, a reflectivity of a surface 102 of the inspection target device 100, determined based on a wavelength of the light reflected from surface 102, may be identified, when the metal layer 200 is formed on the surface 101 of the inspection target device 100 and when the metal layer 200 is not formed on the surface 101 of the inspection target device 100. Here, the metal layer 200 used in this experiment includes gold, and the reflectivity when the width w of a minute pattern 192 formed on the surface of the inspection target device 100 is 250 nm and when the width w of a minute pattern 190-1 to 190-N formed on the surface 101 of the inspection target device 100 is 275 nm may be identified.

According to the graph shown in FIG. 5B, it is shown that when the width w of the minute pattern 192 formed on the surface 101 of the inspection target device 100 varies, the reflectivity of the surface 102 of the inspection target device 100 based on the wavelength of the light varies. Thus, the surface inspection apparatus detects a difference in the reflectivity, to thereby determine whether neighboring minute patterns 190-1 to 190-N are similar to one another. A wavelength section in which the surface inspection apparatus may detect the difference in the reflectivity according to a change of the width w of the minute patterns 190-1 to 190-N, when the metal layer 200 is formed on the surface of the inspection target device 100, is defined as $\Delta\lambda m$ and a wavelength section in which the surface inspection apparatus may detect the difference in the reflectivity according to a change of the width w of the minute patterns 190-1 to 190-N, when the metal layer 200 is not formed, is defined as $\Delta\lambda n$. According to the graph above, the wavelength section $\Delta\lambda m$ when the metal layer 200 is formed may be formed in a greater wavelength area than the wavelength section $\Delta\lambda n$ when the metal layer 200 is not formed.

As described above with reference to FIGS. 4A and 4B, in order to inspect the inspection target device 100 on which patterns 190-1 to 190-Nminuter (e.g., smaller) than previous patterns 190-1 to 190-N are formed, the wavelength area which the surface inspection apparatus may analyze has to be decreased, and thus, a previously used surface inspection apparatus has to be replaced. In some example embodiments, if and/or when the metal layer 200 is formed on the inspection target device 100, the wavelength section $\Delta\lambda m$ in which the change in the reflectivity according to the change in the width w of the minute patterns 190-1 to 190-N is apparent is formed in a great wavelength area. This may be based at least in part upon a surface plasmon effect, including SPR, associated with the irradiation of light on the inspection target device 100 based on the presence of the metal layer 200 thereon. Thus, even if the minute patterns 190-1 to 190-N formed on the inspection target device 100 become minuter, the previously used surface inspection apparatus may continue to be used to determine whether neighboring minute patterns 190-1 to 190-N are similar to one another, based on the presence of the metal layer 200 on the inspection target device 100.

In some example embodiments, the wavelength section $\Delta\lambda m$ when the metal layer 200 is formed may be formed wider than the wavelength section $\Delta\lambda n$ when the metal layer 200 is not formed. Thus, the surface inspection apparatus may easily detect the difference in the reflectivity based on the change of the width w of the minute patterns 190-1 to 190-N.

Figure 6:
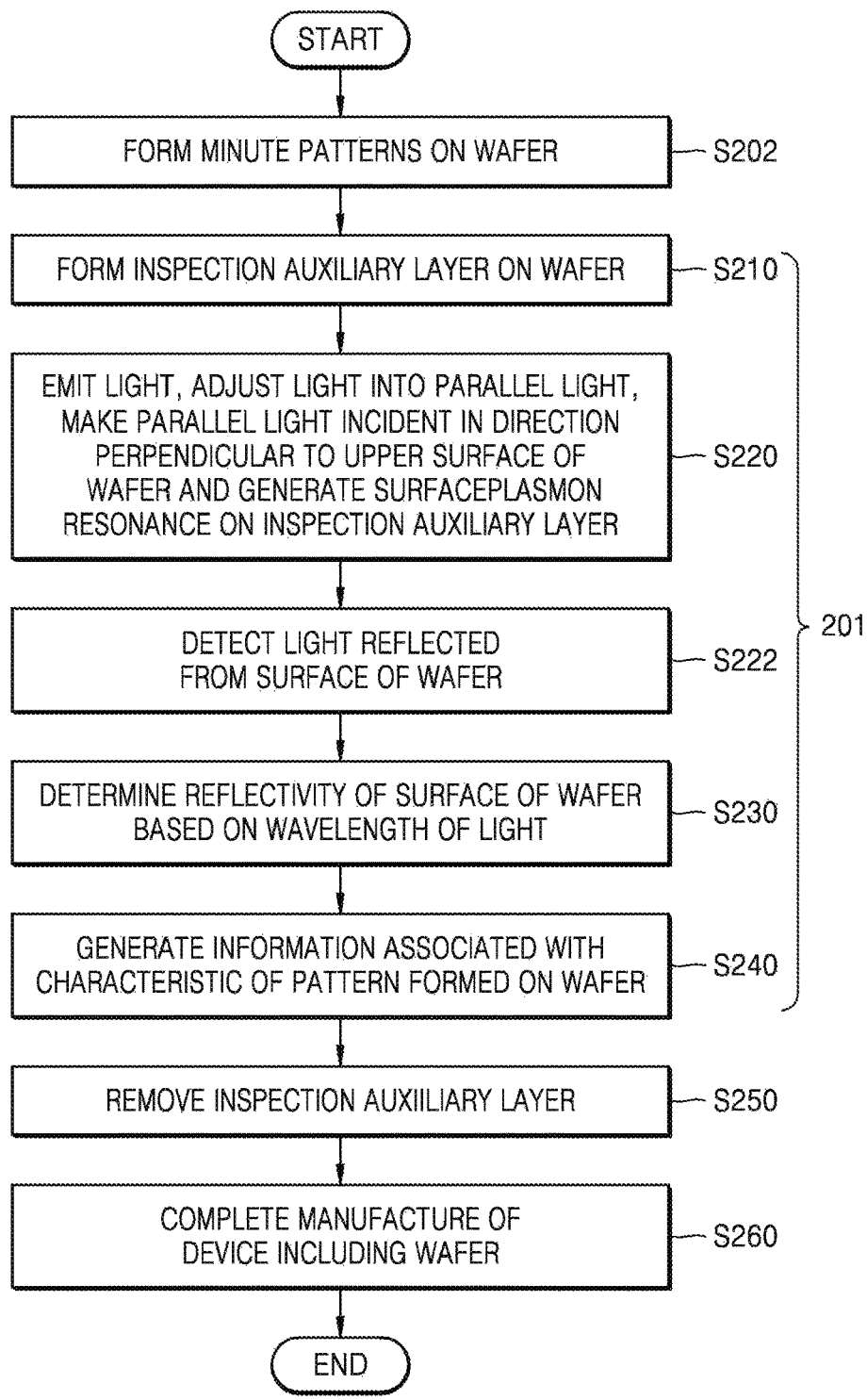
FIG. 6 is a flowchart of a method, according to some example embodiments of the present inventive concepts.

FIG. 6 is a flowchart of a method, according to some example embodiments of the present inventive concepts.

Referring to FIG. 6, the method according to some example embodiments may include forming ("manufacturing") minute patterns on wafer (S202). The method may include inspecting a surface of the wafer (S201). As shown in FIG. 1, the inspecting (S201) may include forming (S210) an inspection auxiliary layer on the wafer and generating (S220) SPR on the inspection auxiliary layer by emitting light for inspecting the surface, adjusting the emitted light into parallel light, and making the parallel light incident in a direction perpendicular to (e.g., normal to) a surface of the wafer. The light used for inspection may be light having a broadband wavelength. Thus, in order to minimize spectrum distortion due to oblique light, the light may be incident in a direction perpendicular to an upper surface of the inspection target device.

As described above, inspecting (S201) may include detecting (S222) light reflected from the surface of the wafer. Determining a reflectivity of a surface of the wafer based on a wavelength of light reflected from the surface of the wafer when the SPR occurs on the inspection auxiliary layer may be different from a reflectivity of light reflected from the surface of the wafer based on a wavelength of the light when the SPR does not occur. Thus, a change in the reflectivity based on the wavelength of the reflected light may be radical, and thus, a range of a wavelength section in which the surface inspection apparatus may detect the change in the reflectivity may correspond to a range of a wavelength section the surface inspection apparatus may be configured to inspect, based on the presence of the inspection auxiliary layer on the wafer. The surface inspection apparatus may determine (S230) the reflectivity of a surface of the wafer (where the surface may be one or more of an outer surface of the wafer and an outer surface of an inspection auxiliary layer formed on the outer surface of the wafer) based on the wavelength of the light reflected from the surface of the wafer. Information associated with a structural characteristic of a pattern formed on the wafer may be generated (S240) based on the determined reflectivity of the surface of the wafer, further based on the wavelength of the reflected light.

The inspection auxiliary layer is formed to improve the surface inspection of the wafer, and may be a metal layer including one or more metals. Preferably, the metal layer may include at least one of metal, silver (Ag), copper (Cu), and aluminum (Al). In some example embodiments, the inspection auxiliary layer is not limited to the metal layer, and may include a non-metal, the real part of a dielectric rate of which is a negative number. The inspection auxiliary layer may be formed via CVD, PVD, ALD, sputtering, E-beam deposition, thermal deposition, or the like. The inspection auxiliary layer may be formed via a combination of the processes described above, or any single process. For the method of inspecting a surface described above, the surface inspection apparatus 300 of FIG. 2A may be used, but it is not limited thereto.

If and/or when wafer is a semiconductor wafer, the forming (S202) may include manufacturing the semiconductor wafer.

As shown in FIG. 6, the method according to some example embodiments may include removing the inspection auxiliary layer (S250), subsequent to the inspecting (S201). As further shown in FIG. 6, the method according to some example embodiments may include manufacturing a device using the wafer (S260), subsequent to the inspecting (S201). The device manufactured at (S260) may include one or more of a semiconductor device, chip device, integrated circuit device, computer device, electronic device, some combination thereof, or the like. In some example embodiments, the wafer may be selectively incorporated into the manufacturing of the device at (S260) based on the information generated at (S240).

Figure 7:
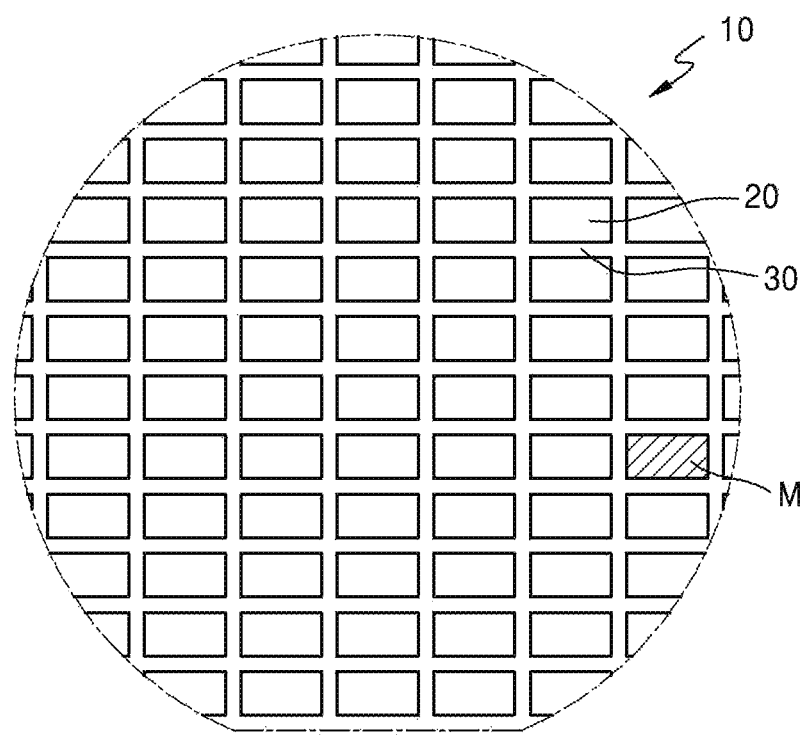
FIG. 7 is a cross-sectional view of an inspection wafer according to some example embodiments of the present inventive concepts.

FIG. 7 is a cross-sectional view of an inspection wafer according to some example embodiments of the present inventive concepts. Aspects that are the same as the aspects of FIG. 6 will not be repeatedly described.

Referring to FIG. 7, the wafer 10 inspected by using a method that includes inspecting a surface according to some example embodiments may include a semiconductor chip area 20 and a scribe lane area 30 dividing adjacent semiconductor chip areas 20. The scribe lane area 30 refers to an area on the wafer 10, on a surface of which horizontal and vertical grooves may be formed via a diamond cutter or a laser beam in order to separate the wafer 10 on which the semiconductor device is formed into a plurality of chips. The wafer 10 having the grooves and on which the semiconductor device is formed may be separated into a plurality of chips. The semiconductor device may be formed in the semiconductor chip area 20.

The wafer 10 may include at least one semiconductor material selected from the group consisting of Si, Ge, SiGe, GaP, GaAs, SiC, SiGeC, InAs, and InP. The wafer 10 may include a rigid substrate, such as a silicon substrate, a silicon on insulator (SOI) substrate, a gallium arsenide substrate, a silicon germanium substrate, a ceramic substrate, a quartz substrate, or a glass substrate for display, or a flexible plastic substrate including polyimide, polyester, polycarbonate, polyethersulfone, polymethylmethacrylate, polyethylene naphthalate, polyethylene terephthalate, etc.

The wafer 10 may include a first conductive type (for example, a p type) substrate. The wafer 10 may be formed by growing a first conductive type (for example, a p type) epitaxial layer and etching the epitaxial layer. Also, the wafer 10 may be formed by etching the first conductive type (for example, the p type) substrate itself.

An inspection auxiliary layer M may be formed on the wafer 10. The inspection auxiliary layer M may be formed on only an area of the wafer 10. Referring to FIG. 7, it is illustrated that the inspection auxiliary layer M, which may be a metal layer, may be formed on a limited portion of the semiconductor chip area 20, which may be a limited portion of a wafer, a limited portion of a surface of an inspection target device, some combination thereof, or the like. In some example embodiments, it is not limited thereto. The inspection auxiliary layer M may be formed on a limited portion of the scribe lane area 30. The inspection auxiliary layer M may be formed on only the area of the wafer 10 via FIB deposition by using a FIB gun.

Figure 8:
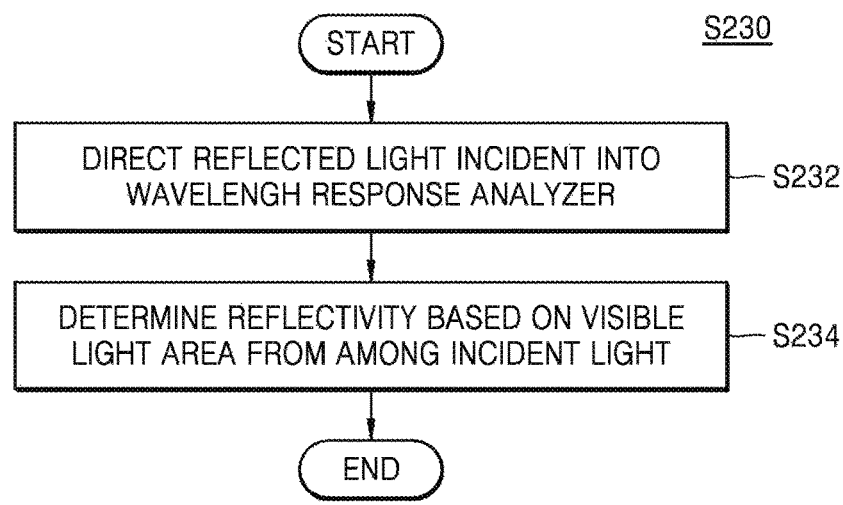
FIG. 8 is a flowchart of a method, according to some example embodiments of the present inventive concepts, and more particularly, a detailed flowchart of operation S230 of FIG. 6.

FIG. 8 is a flowchart of a method, according to some example embodiments of the present inventive concepts, and more particularly, a detailed flowchart of operation S230 of FIG. 6.

Referring to FIG. 8, the method according to some example embodiments may include determining (S230) a reflectivity of light reflected from the wafer 10 based on a wavelength of the light. The obtaining (S230) may include directing (S232) the light reflected from a surface of the wafer 10 incident into a wavelength response analyzer and determining (S234) a reflectivity of a surface of the wafer based on light of a visible light area from among the light incident into the wavelength response analyzer.

As described above with regard to the metal layer 200, a surface plasmon effect, including SPR, may occur on the inspection auxiliary layer M formed on the wafer 10 if and/or when the wafer 10 is irradiated with light. Thus, compared to when inspection is performed on a wafer on which the inspection auxiliary layer M is not formed, the determined reflectivity of the surface of the wafer 10 (e.g., reflectivity associated with the light reflected from the wafer 10) on which the inspection auxiliary layer M is formed, based on the wavelength of the light reflected therefrom, may be changed.

In general, when light is irradiated onto a minute pattern in a nano-unit, which is formed on a wafer, and reflected light is analyzed, a change in a reflectivity associated with the reflected light in a wavelength of an ultraviolet area may be measured to be relatively large. In particular, as the minute pattern becomes minuter, the value of the wavelength in which there is a great change in the reflectivity may decrease. In some example embodiments, when an inspection auxiliary layer M configured to generate the SPR is formed on the wafer 10, the light reflected from the inspection auxiliary layer M may be measured to have a relatively large change in the reflectivity in a visible light area, relative to light reflected from a wafer from which the inspection auxiliary layer is absent. If and when a wavelength area of the light which the wavelength response analyzer may analyze is a visible light area, a wavelength range that the surface inspection apparatus for performing the method of inspecting a surface may correspond to the wavelength range in which there is great change of the reflectivity of the light reflected from the inspection auxiliary layer. Also, since the change in the reflectivity based on the wavelength increases, it may be easy to obtain a wavelength value when the reflectivity has the lowest value. Thus, the surface inspection apparatus may effectively inspect the surface of the wafer.

Figure 9:
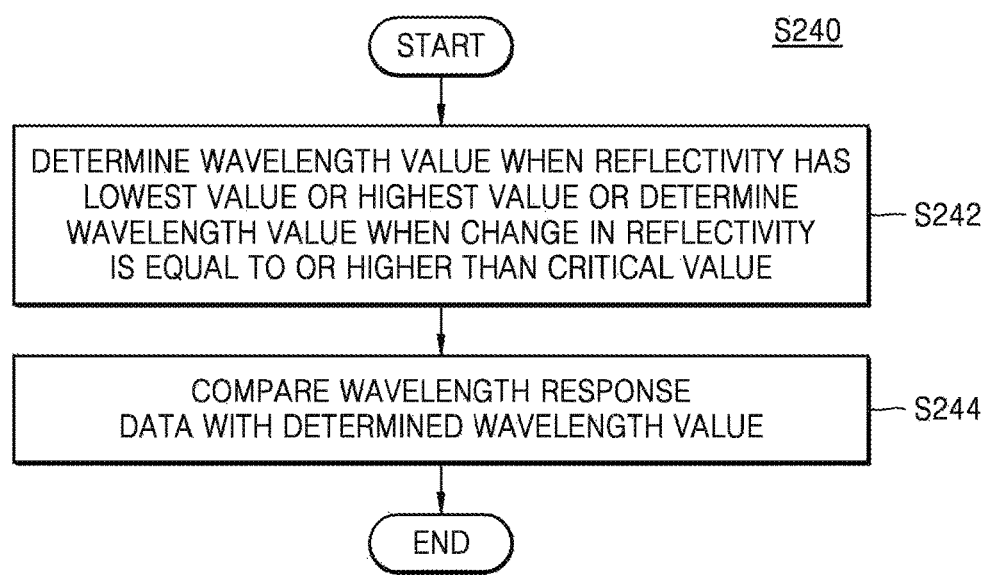
FIG. 9 is a flowchart of a method, according to the present inventive concepts, and more particularly, a detailed flowchart of operation S240 of FIG. 6.

FIG. 9 is a flowchart of a method, according to the present inventive concepts, and more particularly, a detailed flowchart of operation S240 of FIG. 6.

Referring to FIG. 9, the method of inspecting a surface according to some example embodiments may include generating (S240) information associated with a structural characteristic of the pattern formed on the wafer 10. The generating (S240) may include determining a wavelength value when the reflectivity associated with the light reflected from the surface of the wafer 10 based on the wavelength of the light has the lowest value or the highest value, or obtaining (S242) a wavelength value when the change in the reflectivity has a value that is equal to or higher than a critical value. A theoretical model having a pattern having substantially the same shape (e.g., the same shape within manufacturing tolerances and/or material tolerances) as the pattern formed on the wafer 10 may be used and wavelength response data based on a structural characteristic of the theoretical model and the wavelength value may be compared (S244) with each other to determine whether the wavelength response data and the wavelength value correspond with each other. In some example embodiments, wavelength response data and wavelength values that correspond to each other may include wavelength response data and wavelength values that match within a particular margin (e.g., 10% margin of error between wavelength response data and wavelength values). In some example embodiments, wavelength response data and wavelength values that correspond to each other include wavelength response data and wavelength values that are the same or substantially the same (e.g., the same within manufacturing tolerances and/or material tolerances).

Here, the critical value may be a value that may be configured by a user. Also, the critical value may be a minimum change in the reflectivity, which is appropriate for the surface inspection apparatus used for surface inspection, in order to compare the wavelength response data and the wavelength value.

The theoretical module may be a sample on which surface inspection is performed before the method of inspecting a surface according to some example embodiments is performed, and the sample may have a minute pattern having substantially the same shape (e.g., the same shape within manufacturing tolerances and/or material tolerances) as the minute pattern formed on the wafer 10. A surface inspection result according to the structural characteristic of the theoretical model may be stored in a library. Accordingly, when the method of inspecting a surface according to some example embodiments is performed and reflectivity data based on the wavelength of the light reflected from the surface of the wafer is derived, the reflectivity data may be compared with wavelength response data of the theoretical model stored in the library. Accordingly, the information associated with the structural characteristic of the pattern formed on the wafer 10, that is, the information associated with the width and the height of the pattern, and the distance between the patterns may be obtained.

In some example embodiments, a wafer 10 may be selectively incorporated into the manufacture of a device at (S260) based on the generated information. For example, the wafer 10 may be incorporated into the manufacturing of the device at (S260), such that the wafer 10 is incorporated into the manufactured device, based on information generated at (S240) according to a determination at (S244) that wavelength response data based on a structural characteristic of the theoretical model and the wavelength value correspond to each other. In another example, the wafer 10 may be restricted from being incorporated into the manufacturing of the device at (S260), such that the wafer 10 is not incorporated into the manufactured device, based on information generated at (S240) according to a determination at (S244) that wavelength response data based on a structural characteristic of the theoretical model and the wavelength value do not correspond to each other.

While the inventive concepts have been particularly shown and described with reference to embodiments thereof, it will be understood that various changes in form and details may be made therein without departing from the spirit and scope of the following claims.

What is claimed is:

1. A method, comprising:
    forming a metal layer on a surface of an inspection target device, the inspection target device including a pattern, such that the metal layer is formed on the pattern and an outer surface of the metal layer is distal to the surface of the inspection target device;
    emitting light incident on the outer surface of the metal layer, and adjusting the emitted light to be incident to the outer surface of the metal layer and normal to the outer surface of the metal layer;
    detecting a spectrum of the light reflected from the outer surface of the metal layer; and
    generating, based on the detected spectrum, information associated with a structural characteristic of the pattern formed on the surface of the inspection target device,
    wherein the pattern includes a plurality of patterns, the patterns being spaced apart according to a particular period,
    wherein the generating includes measuring a width of at least one pattern of the plurality of patterns and a distance between adjacent patterns, based on a material of the metal layer.

2. The method of claim 1, wherein the generating includes,
    comparing the detected spectrum with a theoretical spectrum of a theoretical model, the theoretical model having a pattern having a substantially common shape in relation to the pattern formed on the inspection target device; and
    determining whether a characteristic of the theoretical spectrum corresponds to a characteristic of the detected spectrum, based on the comparing.

3. The method of claim 1, wherein the generating includes determining a similarity between adjacent patterns.

4. The method of claim 1, wherein the metal layer has a thickness that is less than half of a distance between adjacent patterns.

5. The method of claim 1, wherein the generating includes calculating an error associated with the metal layer.

6. The method of claim 5, wherein the calculating the error includes calculating the error based on,
    the width of the at least one pattern,
    a height of the at least one pattern,
    the distance between adjacent patterns, and
    a material of the metal layer.

7. The method of claim 1, wherein the metal layer includes at least one of Au, Ag, Cu, and Al.

8. A method, comprising:
    detecting light reflected from a metal layer on a surface of an inspection target device, the inspection target device including at least one pattern, the reflected light being a reflected beam of light incident on the surface of the metal layer;
    determining a spectrum of the light reflected from the surface of the metal layer on the inspection target device;

generating, based on the determined spectrum, information associated with a structural characteristic of the at least one pattern formed on the surface of the inspection target device; and forming a semiconductor device, using the inspection target device, based on the information associated with the structural characteristic of the pattern, the forming the semiconductor device including
forming one or more layers on a substrate, and
removing at least portions of the one or more layers to form a structure, wherein the at least one pattern includes a plurality of patterns, the plurality of patterns being spaced apart according to a particular period, wherein the generating includes measuring a width of at least one pattern of the plurality of patterns and a distance between adjacent patterns, based on, a material of the metal layer.

9. The method of claim 8, further comprising:
removing the metal layer from the inspection target device based on the information associated with the structural characteristic of the pattern, prior to forming the semiconductor device using the inspection target device.

10. The method of claim 8, wherein,
the generating includes,
comparing the determined spectrum with a theoretical spectrum of a theoretical model, the theoretical model having a pattern having a substantially common shape in relation to the pattern formed on the inspection target device, and
determining whether a characteristic of the theoretical spectrum corresponds to a characteristic of the determined spectrum, based on the comparing, and
the forming includes,
selectively incorporating the inspection target device into the semiconductor device based on the determining of whether the characteristic of the theoretical spectrum corresponds to the characteristic of the determined spectrum.

11. The method of claim 8, wherein the metal layer is on a limited portion of the surface of the inspection target device.

* * * * *